United States Patent [19]

Kawamoto et al.

[11] 4,220,915
[45] Sep. 2, 1980

[54] RESISTIVITY MEASUREMENT SYSTEM

[75] Inventors: Hirohisa Kawamoto, Princeton, N.J.; Elmer L. Allen, Jr., Philadelphia, Pa.

[73] Assignee: RCA Corporation, New York, N.Y.

[21] Appl. No.: 920,077

[22] Filed: Jun. 28, 1978

[51] Int. Cl.² ............... G01R 27/04; G01R 27/02
[52] U.S. Cl. ........................... 324/58 A; 324/62
[58] Field of Search ............... 324/58.5 A, 58 A, 62

[56] References Cited

U.S. PATENT DOCUMENTS

| | | | |
|---|---|---|---|
| 3,054,948 | 9/1962 | Rymaszewski | 324/58 A |
| 3,155,898 | 11/1964 | Chope | 324/58.5 A |
| 3,169,168 | 2/1965 | Capranica | 324/62 X |
| 3,237,058 | 2/1966 | Andregg | 324/64 X |
| 3,501,692 | 3/1970 | Kluck | 324/58.5 A |
| 3,681,684 | 8/1972 | Busker et al. | 324/58.5 A |
| 3,811,087 | 5/1974 | Schmelzer | 324/58.5 A |
| 3,815,019 | 6/1974 | Wiles | 324/58.5 A |
| 3,851,244 | 11/1974 | Mounce | 324/58.5 A |
| 3,903,477 | 9/1975 | Cronson et al. | 324/58.5 A |
| 3,993,947 | 11/1976 | Maltby et al. | 324/58 A X |

FOREIGN PATENT DOCUMENTS

| | | | |
|---|---|---|---|
| 1320673 | 6/1973 | United Kingdom | 324/58.5 A |
| 226899 | of 1969 | U.S.S.R. | 324/58.5 A |
| 397858 | 9/1973 | U.S.S.R. | 324/58 A |

Primary Examiner—Ernest F. Karlsen
Attorney, Agent, or Firm—E. M. Whitacre; J. S. Tripoli

[57] ABSTRACT

A system for measuring the bulk resistivity or sheet resistance of a sample of material includes a source of r.f. signals, a transmitting device and receiving device. The sample is placed between the transmitter and the receiver. A display is used to monitor the amplitude characteristic of the received r.f. signal at a particular frequency. The amplitude characteristic at the particular frequency is a measure of the bulk resistivity of the sample of the material.

5 Claims, 3 Drawing Figures

RESISTIVITY MEASUREMENT SYSTEM

The present invention relates generally to a system for measuring the bulk resistivity or sheet resistance of materials and more particularly to the use of r.f. signals and techniques for performing such a measurement.

There are many applications where it is desirable to determine the bulk resistivity or the sheet resistance of a given material. One such application arises in the field of video disc manufacturing. The discs may be of the type described in U.S. Pat. No. 3,842,194 to J. K. Clemens, that is a disc comprising a metalized base material having a dielectric coating thereon, or, the disc may be of some other construction such as comprising an uncoated carbon filled material.

These discs are neither pure conductors nor pure insulators. Discs of the aforementioned type have been found to be useful in capacitive pickup video disc record and playback systems such as the system described in U.S. Pat. No 3,842,194, where signals are recorded in the form of geometric variations in the bottom of a spiral groove on the surface of the disc.

In respect of the carbon filled material type disc, by way of example, it has been determined that the bulk resistivity of this material has a direct correlation to the carrier to noise ratio encountered during the playback of the disc. There are, of course, other factors which will affect the carrier to noise ratio of the final disc product such as the depth of the geometric variations and the physical sharpness of the geometric variations to name but two of such other factors. However, assuming all other factors meet the desired specifications, one can determine whether or not a given video disc will fail to meet final carrier to noise requirements if it fails to meet certain initial bulk resistivity requirements.

In the case of carbon filled uncoated video discs, for example, it has been determined that the record should have a bulk resistivity of something less than about 5 ohm-centimeters in order to achieve a carrier to noise ratio of about 48 dB or greater.

Even before processing an entire batch of carbon filled material into disc form, it is desirable to select samples of the mix and conduct the bulk resistivity test to guard against the inadvertent contamination of the raw materials before the manufacturing process.

One approach to the measurement of bulk resistivity is to utliize a microwave network analyzer. In this approach a small circular sample is cut out of a disc and placed in a special holder which is attached to the machine. Reflection measurements are then made at various microwave frequencies and the results are plotted on a Smith chart. The resistive element at the frequency of interest may then be obtained. The primary disadvantage of this approach is that a disc is destroyed and, in addition, it is a time consuming task not suitable for a large manufacturing operation.

The present invention provides a means for measuring bulk resistivity or sheet resistance which is essentially non-contacting with the test sample, non-destructive in nature, and can be performed in a relatively short period of time.

In accordance with the present invention for measuring the resistivity of a sample of material, an r.f. signal is provided with an appropriate transmitting means. Means are also provided for receiving this r.f. signal. The sample of material to be tested is retained in a means located between the transmitting means and the receiving means. The retaining means is electrically connected to the sample and to a point of reference potential. A display means is coupled to the receiving means for displaying the amplitude characteristic of the received r.f. signal. The displayed amplitude characteristic provides a measure of bulk resistivity of the sample of material.

Figure 1:
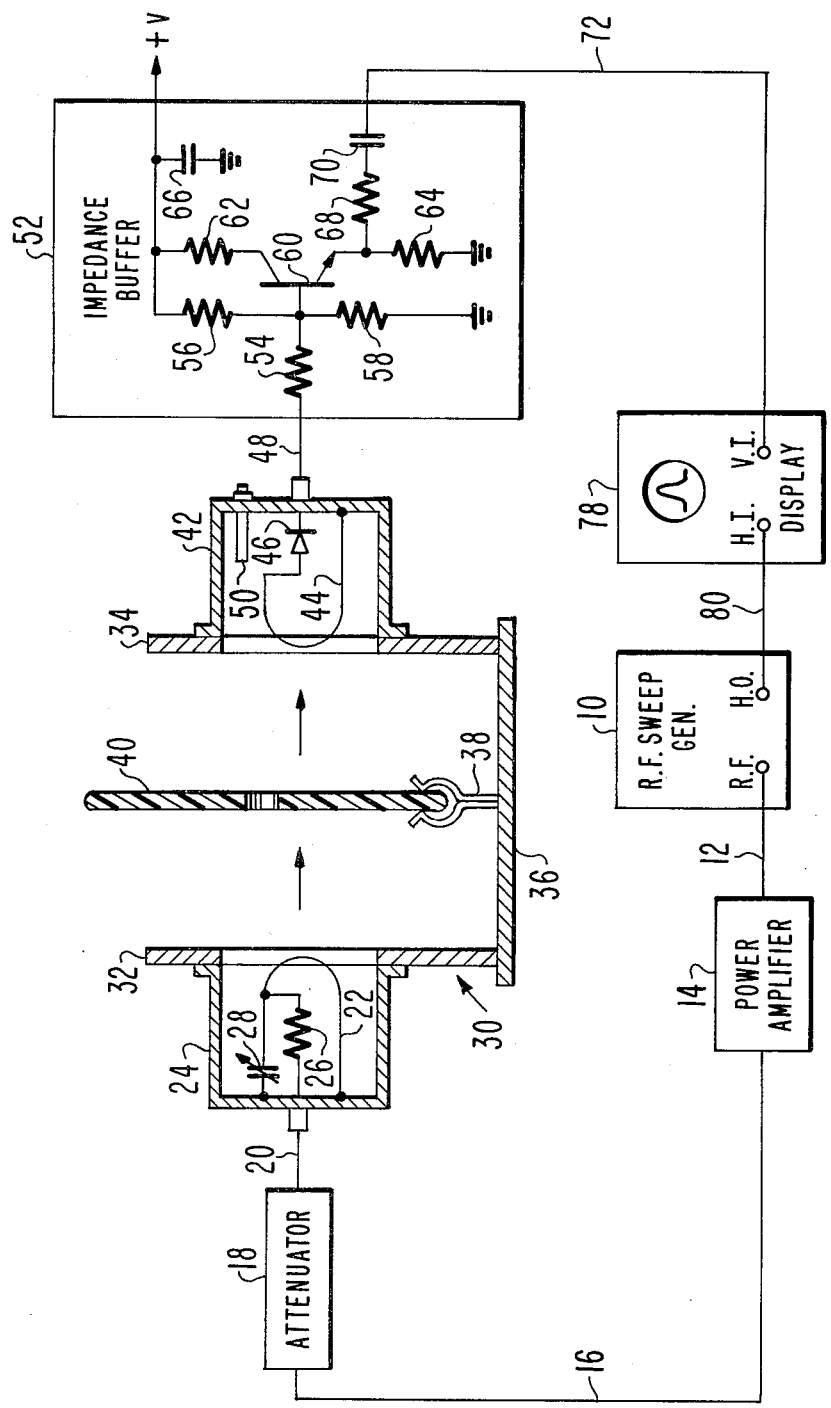
FIG. 1 is a partial mechanical and partial schematic diagram of one embodiment of the present invention.
Figure 3:
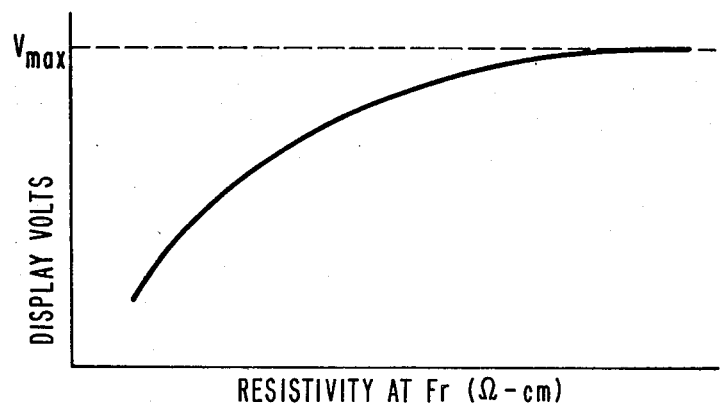

FIG. 3 is a graph showing the relationship between the amplitude of the received r.f. signal and the bulk resistivity of the sample of material for the embodiment shown in FIG. 1; and In FIG. 1, an r.f. sweep generator 10 provides an r.f. signal across a band of frequencies at an r.f. output terminal. In the embodiment illustrated, r.f. generator 10 is set to sweep the frequency band from 720 MHz to 1500 MHz. The output power curve from generator 10 across the swept frequency band is substantially constant. The r.f. output terminal of generator 10 is coupled via a coaxial cable 12 to a power amplifier 14. Amplifier 14 permits the adjustment of the swept r.f. signal power level to any desired level. The r.f. signal from amplifier 14 is coupled via another coaxial cable 16 to an attenuator 18. Attenuator 18 is used to fine tune the power adjustment across the band of frequencies.

The swept r.f. signal is coupled via another coaxial cable 20 to a transmitting loop antenna 22 which is enclosed in a metal box-like chamber 24. One face of the box-like chamber 24 is open for purposes of transmitting the r.f. signal. The transmitting loop antenna 22 also comprises a resistor 26 connected between the center conductor of the coaxial cable 20 and the material forming the loop antenna 22. A variable capacitor 28 is connected between the junction of resistor 26 and loop 22 and the box 24, i.e., between the aforesaid junction and the system ground potential. The other end of the loop 22 is also connected to a point of ground potential. In the embodiment of FIG. 1, resistor 26 is approximately 51 ohms and variable capacitor 28 is adjustable between approximately 4 and 6 pf.

Capacitor 28 and resistor 26 are provided for purposes of tuning the transmitting loop antenna to a frequency of 915 MHz. This frequency is selected because it is the frequency at which the pickup arm of the aforementioned video disc system operates and therefore, is the primary frequency of interest at which the bulk resistivity of the sample of material under test is to be measured.

The box-like member 24 is connected to a metal fixture shown generally as 30 which comprises two parallel plates 32 and 34 connected to a flat base member 36. A sample retaining mechanism 38 is connected to the base 36. The base 36, retainer 38 and plates 32 and 34 are all at the system ground potential. Retaining mechanism 38, in the embodiment of FIG. 1, is in the form of a plurality of spring-like, electrically conductive fingers which are arranged to spread apart upon insertion of the sample to be tested. The spring tension of the fingers in combination with the test fixture 30 serve to retain the sample in an upright position.

In FIG. 1, the sample under test is a video disc record 40. Record 40, when placed in retainer 38 is positioned in the transmission path of loop antenna 22. Retainer 38 is arranged to have its spring-like fingers grasp the record 40 in the preplay area where information has not been recorded, or will not be recorded if the sample is a blank. This arrangement prevents imparting undesirable scratches on the playback area of the record.

A metal box-like structure 42 is located on the plate member 34. Structure 42 is enclosed on all sides except the face which is positioned adjacent the record 40 and in line with the transmission path of the transmitted signal from loop antenna 22, through an opening in plate 32, past the record 40 and through a corresponding opening in plate 34.

A receiving loop antenna 44 is located inside of structure 42. Antenna 44 is connected to structure 42 on one end and connected to the anode of a diode detector 46 on the other end. The cathode of diode 46 is connected to the center conductor of another coaxial cable 48. Also included within the structure 42 is a threaded screw member 50 which functions as a trimmer capacitor in the receiver antenna microwave circuit. Trimmer capacitor 50 is adjusted such that the receiving antenna circuit is resonant at 915 MHz.

The center conductor of cable 48 is connected to an impedance buffer 52 which is used to isolate the receiver microwave circuit from the display device 78. Buffer 52 comprises a resistor 54 connected on one side to the center conductor of cable 48 and on the other side to the junction between resistors 56 and 58. Resistors 56 and 58 are connected between a source of bias potential $+V$ and ground potential. The base electrode of a transistor 60 is connected to the aforementioned junction between resistors 56 and 58. The collector electrode of transistor 60 is connected, via resistor 62, to the $+V$ supply voltage. The emitter electrode of transistor 60 is connected, via resistor 64, to a point of ground potential. Capacitor 66 is connected between the $+V$ supply voltage and a point of ground potential. Transistor 60 is arranged in an emitter follower configuration and the output signal from the emitter electrode is coupled via the series combination of resistor 68 and capacitor 70 to the display device 78 via conductor 72. The signal picked up by receiving loop antenna 44, detected by diode 46, and buffered by impedance buffer 52 is supplied to the vertical input terminal of an oscilloscope which functions as the display device 78. The horizontal input signal to the display device 78 is provided via conductor 80 from the horizontal output terminal of the r.f. sweep signal generator 10.

Figure 2:
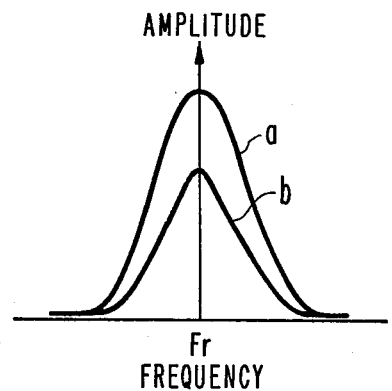
FIG. 2 is a representation of waveforms appearing on the display device in the embodiment shown in FIG. 1.

In the operation of the embodiment of the invention shown in FIG. 1, the system is initially set up by transmitting the r.f. sweep signal from the transmitting antenna 22 to the receiving antenna 44 in the absence of any sample in the retainer 38. The display device 78 will show a waveform such as (a) in FIG. 2. The resonant peak of the waveforms is at the tuned frequency of 915 MHz, both the transmitting antenna 22 and the receiving antenna 44 having been tuned to this frequency. This sets the upper amplitude level on the display for the given system based on such factors as the distance between the antennas 22 and 44, the power levels employed and even the materials used to construct the system. The sample, such as record 40, is then inserted into the retainer 38 between the two antennas 22 and 44. The scope display device 78 now shows a waveform such as (b) in FIG. 2. The peak is still at the resonant frequency of 915 MHz. The new amplitude of the waveform (b) at the resonant frequency, Fr, is a measure of the bulk resistivity of the sample under test.

It will be recalled that the sample to be tested is neither a perfect conductor nor a perfect insulator at the frequency of interest, i.e., Fr=915 MHz. If a perfect conductor were to be placed in the retainer 38, little if any r.f. energy would be received by antenna 44 and the amplitude of waveform (b) in FIG. 2 would be at or close to zero. If a perfect insulator were placed in retainer 38, substantially all of the r.f. energy would be received at the antenna 44 and the amplitude of waveform (b) would not change to any substantial degree. When a carbon filled material, such as that used in certain forms of record 40, is inserted in retainer 38, it is believed that r.f. currents are induced on the surface of the material which flow to the ground potential and thus the amount of energy absorbed or blocked out by the sample of material and hence the drop in the amplitude of the received waveform shown on the display 78 is a measure of the bulk resistivity of the material being tested. It has further been found that, in the absence of electrically grounding the sample under test, the amplitude readings do not consistently correspond to the resistivities measured.

The graph of FIG. 3 shows a typical curve which relates the display voltage to the resistivity of a carbon filled material used to form a video disc. Both the ordinate and the abscissa scales of FIG. 3 happen to be logarithmic scales for the embodiment described in connection with FIG. 1. FIG. 3 shows that as the resistivity gets very high, i.e., tending toward an insulator, the amplitude of the display, at the frequency Fr, approaches a maximum value. This maximum value is the reading obtained in the absence of a sample when transmitting the r.f. signal through air. As the resistivity goes down the peak amplitude of the display voltage goes down toward zero for the very low resistivity values of good conductors at the frequency Fr. The peak amplitude of the display voltage between the maximum voltage and very low voltage levels provides a good measure of the resistivity of the sample. In operation one can simply read the peak voltage of the display and obtain the corresponding resistivity of the sample from a graph such as that of FIG. 3, or, if desired one can calibrate the voltage scale of the display 78 to read out the resistivity directly in ohms-cm.

The measurement apparatus described above has been found to be useful to check for bulk resistivity of samples of material other than in the form of discs such as record 40. Samples of material before being pressed into disc form may be measured so that the manufacturing process is not initiated in the event that the sample shows a bulk resistivity greater than a prescribed level.

The present invention, as illustrated in the embodiment described herein, provides a fast, economical, non-destructive, basically non-contacting (in the playback area of a video disc record) technique for measuring bulk resistivity.

What is claimed is:

1. A system for measuring the resistivity of a substantially rigid sample of material having first and second major surfaces parallel to each other, the length of said sample in a plane parallel to said major surfaces being substantially greater than the width of said sample taken in a plane perpendicular to said major surfaces, said system comprising:

an assembly comprising a first conductive wall, a second conductive wall parallel to said first wall and spaced a given distance from said first wall, a conductive base connecting said first and second conductive walls, each of said first and second conductive walls having an aperture and each wall further having a conductive enclosure surrounding the corresponding aperture;

a sweep frequency generator for providing an r.f. signal whose frequency varies across a given band of frequencies including a particular frequency;

means for providing the unguided transmission of said r.f. signal including a transmitting antenna, said transmitting antenna being enclosed in said first wall conductive enclosure such that said r.f. signal is transmitted through the first wall aperture;

means for receiving said r.f. signal including a receiving antenna, said receiving antenna being enclosed in said second wall conductive enclosure such that said r.f. signal is received through said second wall aperture;

conductive means connected to said conductive base between said first and second walls and extending from said base to a level below the apertures in said first and second walls, said conductive means being arranged for retaining said sample of material such that said sample of material is held parallel to said first and second walls and for retaining said sample of material in a position whereby a substantial portion of said sample of material is in the path of said transmitted r.f. signal, said conductive retaining means, said base and said first and second walls being at ground potential;

detector means connected to said receiving antenna and located within said second wall enclosure for detecting said r.f. signal; and display means coupled to said detection means and to said r.f. sweep generator for displaying the amplitude characteristic of the detected r.f. signal, said amplitude characteristic providing a measure of the resistivity of said sample of material.

2. The system according to claim 1, wherein said transmitting antenna comprises a tunable loop antenna tuned to said particular frequency and wherein said system further comprises a tuning means located substantially within said first wall enclosure for tuning said transmitting loop antenna.

3. The system according to claim 2, wherein said receiving antenna comprises a tunable loop antenna tuned to said particular frequency and wherein said system further comprises a receiving antenna tuning means located substantially within said second wall enclosure for tuning said receiving loop antenna.

4. The system according to claim 3, wherein said conductive retaining means comprises spring-like conductive fingers for receiving said sample of material.

5. The system according to claim 4, wherein said sample of material comprises a disc-like record.

* * * * *